United States Patent
Liu (10) Patent No.: US 9,451,885 B2
(45) Date of Patent: Sep. 27, 2016

(54) DEPTH-SELECTIVE FIBER-OPTIC PROBE

(75) Inventor: Yang Liu, Sewickley, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 327 days.

(21) Appl. No.: 13/991,459

(22) PCT Filed: Dec. 15, 2011

(86) PCT No.: PCT/US2011/065226
§ 371 (c)(1),
(2), (4) Date: Sep. 16, 2013

(87) PCT Pub. No.: WO2012/087754
PCT Pub. Date: Jun. 28, 2012

(65) Prior Publication Data
US 2014/0249427 A1 Sep. 4, 2014

Related U.S. Application Data

(60) Provisional application No. 61/426,077, filed on Dec. 22, 2010.

(51) Int. Cl.
| | |
|---|---|
| *A61B 5/00* | (2006.01) |
| *A61B 1/00* | (2006.01) |
| *A61B 1/07* | (2006.01) |
| *A61B 5/1455* | (2006.01) |
| *G01N 21/47* | (2006.01) |
| *G02B 6/32* | (2006.01) |

(52) U.S. Cl.
CPC ........... *A61B 5/0084* (2013.01); *A61B 1/0017* (2013.01); *A61B 1/00096* (2013.01); *A61B 1/00167* (2013.01); *A61B 1/00188* (2013.01); *A61B 1/07* (2013.01); *A61B 5/0075* (2013.01); *A61B 5/1455* (2013.01); *A61B 5/443* (2013.01); *A61B 5/444* (2013.01); *G01N 21/474* (2013.01); *A61B 2560/0233* (2013.01); *G01N 2021/4742* (2013.01); *G01N 2201/0639* (2013.01); *G02B 6/32* (2013.01); *Y10T 29/49826* (2015.01)

(58) Field of Classification Search
CPC .............. A61B 5/0075; A61B 5/0084; A61B 1/00096; G01N 2021/4742; G01N 2201/0639
See application file for complete search history.

(56) References Cited

U.S. PATENT DOCUMENTS

| | | | | |
|---|---|---|---|---|
| 6,091,984 | A * | 7/2000 | Perelman et al. | 600/476 |
| 6,421,549 | B1 * | 7/2002 | Jacques | 600/331 |
| 6,922,583 | B1 | 7/2005 | Perelman et al. | |
| 7,139,076 | B1 * | 11/2006 | Marbach | 356/446 |
| 7,937,226 | B2 | 5/2011 | Amelink et al. | |
| 2004/0073120 | A1 * | 4/2004 | Motz | A61B 5/0075 600/478 |

(Continued)

*Primary Examiner* — Baisakhi Roy
(74) *Attorney, Agent, or Firm* — Kegler Brown Hill & Ritter; James J. Pingor (57) ABSTRACT

Systems and methods that facilitate analysis of superficial tissue based at least in part on a depth-selective fiber optic probe are discussed herein. The depth-selective fiber optic probe can include an illumination fiber for providing light to the superficial tissue, a collection fiber for collected reflected light, a ball lens that couples the fibers, and a protective overtube that houses the ball lens and fibers. The distances between the ball lens and fibers and between the fibers can be optimized based on several factors, such as by minimizing the illumination spot size, maximizing the overlap between the illumination and collection spots, and based on the angle between the illumination and collection beams.

14 Claims, 9 Drawing Sheets

(56) References Cited

U.S. PATENT DOCUMENTS

| | | | |
|---|---|---|---|
| 2007/0129615 A1* | 6/2007 | Backman et al. | 600/315 |
| 2009/0062642 A1* | 3/2009 | Hauck | 600/429 |
| 2010/0165339 A1* | 7/2010 | Morgan et al. | 356/318 |
| 2013/0303861 A1* | 11/2013 | Backman et al. | 600/301 |

* cited by examiner

DEPTH-SELECTIVE FIBER-OPTIC PROBE

CROSS-REFERENCE TO RELATED APPLICATIONS

This application claims the benefit of U.S. Provisional Patent application Ser. No. 61/426,077 entitled "A DEPTH-SELECTIVE FIBER-OPTIC PROBE FOR CHARACTERIZATION OF SUPERFICIAL TISSUE WITH A CONSTANT PHYSICAL DEPTH" and filed Dec. 22, 2010. The entirety of the above-noted application is incorporated by reference herein.

NOTICE ON GOVERNMENT FUNDING

This invention was made with government support by the National Institutes of Health (NIH) and NIH Skin Cancer SPORE (P50CA121973). The government has certain rights in the invention.

BACKGROUND

The in vivo characterization of superficial tissue is of significant importance for many biomedical applications, such as cancer detection, and investigation of skin pigmentation and hydration. Due to the multi-layered structures of most biological tissue, the characterization of the avascular superficial epithelium is often confounded by the contribution of the scattering and absorption from the underlying connective tissue and blood vessels. To selectively assess the superficial tissue, the depth-selective measurement is crucial to distinguish photons originating in the superficial tissue from those propagating into the deeper tissue.

Reflectance spectroscopy has been widely used to probe tissue properties in vivo, often implemented via a compact fiber optic probe with well-controlled source and detection fiber separations, typically in the ranges from several hundred microns to a few millimeters. They generally assess the entire epithelium and the underlying connective tissue in conjunction with a variety of blood vessels such as capillaries, venules and arterioles. In order to achieve a short penetration depth for superficial epithelium, several strategies have been proposed in conventional systems that have reduced the multiply-scattered photons from the deeper tissue layers and improved the sensitivity to the superficial tissue to some extent.

However, several challenges remain in the development of fiber-optic probes that can selectively characterize the superficial epithelium without being confounded by the underlying connective tissue and blood vessels, while still maintaining a high signal collection efficacy. First, since most epithelial tissues are relatively thin (ranging from 20 to 200 microns), it is difficult to achieve such a short penetration depth for most fiber-optic probe designs. Second, the reduction of fiber core diameter will significantly reduce the efficacy of reflectance signal collection. Third, although the use of fiber-coupling optics such as gradient-index lenses could reduce the probing depth, if the source-detection fibers are positioned at a close distance, the fiber-coupling optics often introduces a significant specular reflection that strongly interferes with the collected signals from tissue.

Furthermore, the determination of optical properties of biological tissue is often complicated by the dependence of penetration depth and sampling volume on tissue scattering coefficient and anisotropy factor of biological tissue. In general, smaller scattering coefficient and higher anisotropy factor will result in a deeper penetration depth and larger sampling volume, leading to inaccurate estimation of absorber content. In other words, the intrinsic variation of tissue optical properties could introduce significant uncertainties in measuring absorber concentrations in turbid media. Thus, it is highly desirable to design an optical probe whose penetration depth is independent of scattering properties of the medium. Although at least one conventional system has included the choice of a "magic" source-detector separation distance of 1.7 mm for a nearly constant optical path length independent of scattering properties, the relatively deep sampling depth of that system is unsuitable for assessing superficial tissue.

SUMMARY

The following presents a simplified summary of the innovation in order to provide a basic understanding of some aspects of the innovation. This summary is not an extensive overview of the innovation. It is not intended to identify key/critical elements of the innovation or to delineate the scope of the innovation. Its sole purpose is to present some concepts of the innovation in a simplified form as a prelude to the more detailed description that is presented later.

The innovation disclosed and claimed herein, in aspects thereof, comprises systems and methods related to fabricating a depth-selective probe. The probe can include an illumination fiber that can be a multi-mode optic fiber, and can include a collection fiber that can be a multi-mode optic fiber. Additionally, the probe can include a ball lens that can couple the illumination fiber and collection fiber, and a protective overtube that can house the illumination fiber, the collection fiber, and the ball lens. In aspects, the arrangement of the ball lens and fibers can facilitate a constant penetration depth.

In another aspect of the subject innovation, it can comprise a method of fabricating a depth-selective probe. The method can include the acts of selecting at least two multi-mode fibers, which can be based at least in part on one or more properties of the at least two multi-mode fibers, and selecting a high-index ball lens. The method can also include a step of arranging the high-index ball lens and the at least two multi-mode fibers within a protective overtube. The high-index ball lens can couple the at least two multi-mode fibers. The arranging step can include the acts of optimizing the distance between the ball lens and the at least two multi-mode fibers, and optimizing the distance between the at least two multi-mode fibers.

To the accomplishment of the foregoing and related ends, certain illustrative aspects of the innovation are described herein in connection with the following description and the annexed drawings. These aspects are indicative, however, of but a few of the various ways in which the principles of the innovation can be employed and the subject innovation is intended to include all such aspects and their equivalents. Other advantages and novel features of the innovation will become apparent from the following detailed description of the innovation when considered in conjunction with the drawings.

DETAILED DESCRIPTION

The innovation is now described with reference to the drawings, wherein like reference numerals are used to refer to like elements throughout. In the following description, for purposes of explanation, numerous specific details are set forth in order to provide a thorough understanding of the subject innovation. It may be evident, however, that the innovation can be practiced without these specific details. In other instances, well-known structures and devices are shown in block diagram form in order to facilitate describing the innovation.

As used in this application, the terms "component" and "system" are intended to refer to a computer-related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

In various embodiments, the subject innovation can include a compact and simple probe design (e.g., a two-channel probe, or other embodiments discussed herein, etc.) optimized for superficial tissue, referred to herein as a depth-selective probe. Systems and methods utilizing such a depth-selective probe can achieve short depth-of-penetration based on multiple features of the depth-selective probe, such as by minimizing the spot size of illumination beam and maximally overlapping the illumination and collection areas through a high-index ball lens, while maintaining high signal collection efficiency without being affected by the notorious specular reflection. In experiments discussed herein, the performance of the depth-selective probe was validated by both numerical simulation and experimental studies with tissue phantoms. These results showed that the depth-selective probe can assess a constant and shallow physical penetration depth, insensitive to a wide range of tissue-relevant scattering coefficients and anisotropy factors, in contrast to conventional probes. These further demonstrate the potential of embodiments of the depth-selective probe to accurately quantify the absorber concentration in superficial tissue without being distorted by tissue scattering properties. The importance of depth-selective probe for superficial tissue is also demonstrated in various human skin sites.

Figure 1:
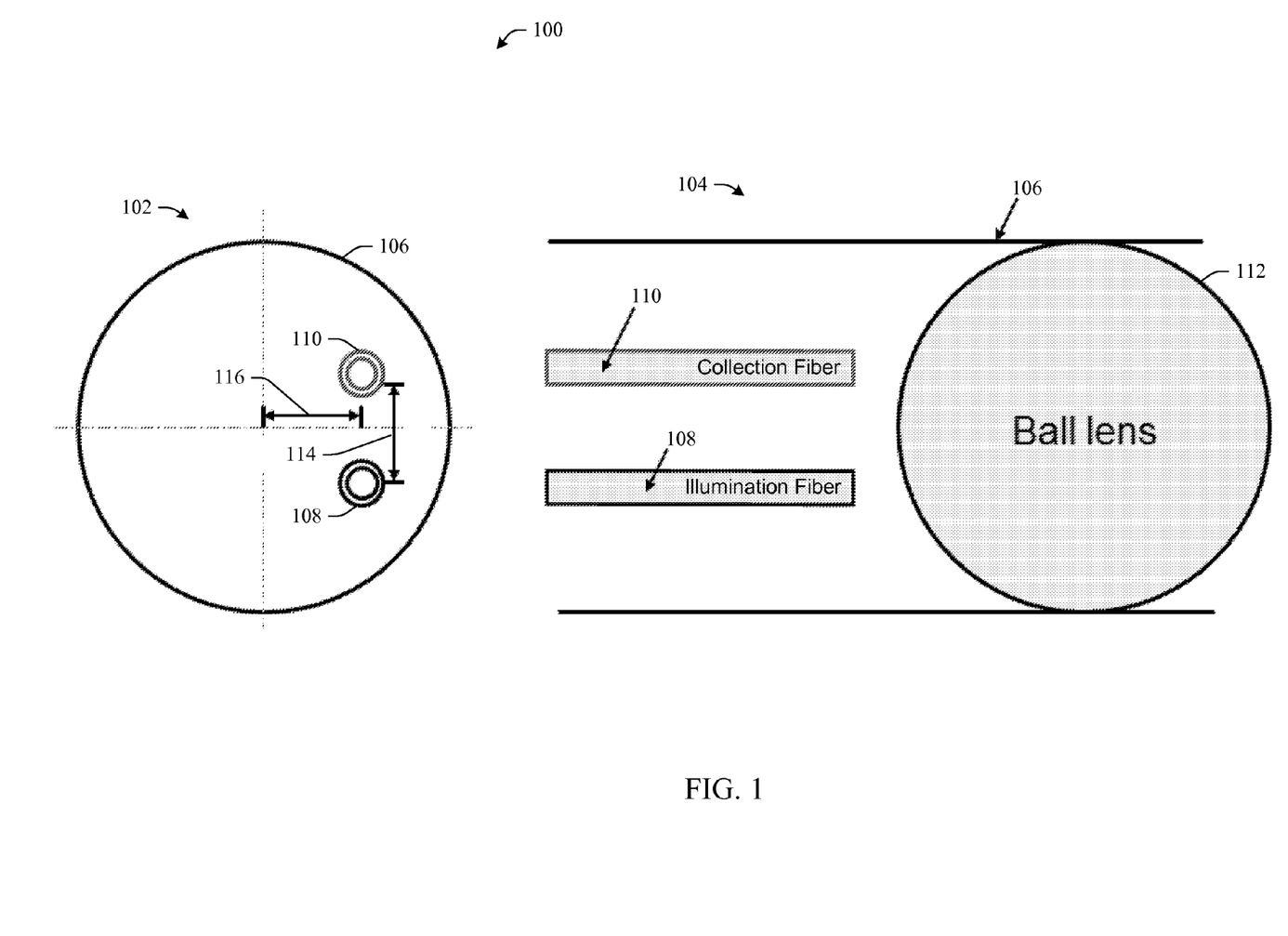
FIG. 1 illustrates a layout of an example depth-selective probe in accordance with aspects of the subject innovation.

Referring initially to the drawings, FIG. 1 illustrates a layout of an example depth-selective probe 100 in accordance with aspects of the subject innovation. Depth-selective probe 100 is illustrated from both a front view 102 and a side view 104. The probe can consist of a protective overtube 106 that can house a plurality of multi-mode optical fibers, with at least one fiber for light illumination (as shown by the example illumination fiber 108 in views 102 and 104) and at least one fiber for light collection (as shown by the example collection fiber 110 in views 102 and 104). In various aspects, probe 100 can comprise two multi-mode fibers, a single illumination fiber 108, and a single collection fiber 110. The multi-mode fibers can be of any of a range of diameters (e.g., 50, 100, or 200 μm-core-diameter, or others, etc.), and can be composed of fused silica fibers or any other material suitable for optical fibers (e.g., silicas, fluorides, phosphates, chalcogenides, plastic optic fibers, etc.). In experiments discussed further herein, the illumination fiber 108 and collection fiber 110 were 200 μm-core-diameter fused silica fibers with a numerical aperture (NA) of 0.22. The multi-mode fibers can be coupled by a high-index (e.g., n=1.85, although a larger or smaller index of refraction can be used in various embodiments, and materials are available for a wide range of indices) ball lens 112 (e.g., with a 2 mm diameter, although a larger or smaller diameter can be used). In experiments discussed herein, the ball lens 112 was a 2 mm diameter Edmund NT45-540 with n=1.85. The optics of probe 100 (e.g., multi-mode fibers, ball lens 112, etc.) can be housed in overtube 106 (e.g., comprised of stainless steel or other suitable material) for protection. For medical applications, the materials can be selected from among those approved by the Food and Drug Administration.

The use of the ball lens 112 can ensure a small illumination spot and maximal overlap between light illumination and collection areas. The distances between the two fibers 114 and the distance between fiber and ball lens 116 can be adjusted to optimize the light collection efficiency and minimize the specular reflection using optical design software (e.g., TracePro 3.22 by Lambda Research, etc.). In the probe used in experiments conducted herein, based on the selections (e.g., of materials, etc.) made for that probe, the optimal distance between the two fibers 114 was 0.625 mm, and the optimal distance 116 was 0.563 mm, as determined by optical design software. This software can use a Monte Carlo simulation (or other techniques intended to be included as alternatives within the term as used herein, such as Morris method, Las Vegas algorithm, etc.) to generate and trace light rays. Additionally, in other aspects, ray tracing can be used. To optimize the properties of illumination and collection spots, each fiber can be assumed to be coupled with an independent light source and a large number of rays (e.g., around $10^5$ rays, etc.) can be launched for each light source in connection with the Monte Carlo simulation. It is to be understood that the specific dimensions provided herein are optimized in light of other system parameters, based on specific criteria relating to increasing the signal to noise ratio, such as one or more of maximizing the overlap between the illumination and detection spots, minimizing specular reflection from the illumination source, etc. The optimization maximizes the overlap between illumination and collection spots while controlling the beam diameter to be as small as possible and/or adopting a large collection angle with respect to the illumination beam.

The system parameters that can affect the specific dimensions provided herein include the indices of refraction and numerical apertures of optical components (e.g., fibers, ball lens, etc.) used in the experiment, and variations in these parameters can result in differing optimization values. Depending on different values of these parameters, the specific values that minimize the background noise and maximize the signal (e.g., by maximizing overlap, etc.) may differ from those specific values discussed above (i.e., that the optimal distance between the two fibers 114 was 0.625 mm, and the optimal distance 116 was 0.563 mm). For example, the ball lens used in the experiment had an index of refraction of 1.85, but other material selections can have widely varying indices, both higher and lower (e.g., various glasses have less than 1.5 or greater than 1.9, and some materials have greater than 2, such as diamond, etc.). In another example, the core fiber diameter for the illumination and collection fibers can be tuned to produce embodiments with different penetration depths. For example, the penetration depth of the embodiment used in the experiments with 200 μm core fiber diameter is approximately 200 μm, but using a smaller (or larger) diameter can produce a shorter (or deeper) penetration depth, such as an approximately 50 μm penetration depth when using fibers with 50 μm core diameter. Although the signal to noise ratio would be worse in a 50 μm core fiber diameter embodiment when compared to the 200 μm, the signal can still be strong enough to be detectable over the noise.

In order to incorporate this depth-selective probe into a reflectance spectroscopy system, the at least one illumination fiber 108 of the probe 100 can be coupled to an illumination source (e.g., halogen lamp, arc lamp (e.g., a hydrargyrum medium-arc iodide (HMI) lamp, etc.), or other sources (e.g., filament, fluorescent lamps, other light sources, etc.), including a gas discharge lamp such as a xenon lamp, for example, a 150 W xenon lamp as used in experiments discussed herein). The collection fiber can be directly connected to a spectrometer or other device capable of capturing and analyzing the collected light. In experiments conducted herein, a spectrometer based on a thermo-electric cooled charge-coupled device (CCD) array was used, configured for wavelengths in the 380 nm to 710 nm range, although other devices or configurations can be used in various embodiments. In aspects, custom-designed software (e.g., using Labview 8.6 interface, etc.) can be used to control the spectrometer for data acquisition.

In other embodiments, the subject innovation can include methods of analyzing superficial tissue (e.g., internally or externally) via a depth-selective probe. For example, illumination light can be produced by an illumination source and transmitted via a first multi-mode fiber (e.g., illumination fiber 108), refracted by a ball lens, and reflected from superficial tissue. The reflected light can be refracted by the ball lens, and collected by a second multi-mode fiber (e.g., collection fiber 110). The collected light can be analyzed by a spectrometer or other device capable of capturing and analyzing the collected light.

In further embodiments, the subject innovation can include one or more methods for fabricating a depth-selective probe. Such a method can include the act of selecting at least two multi-mode fibers based at least in part on one or more properties of the at least two multi-mode fibers. These properties can include a core fiber diameter and a numerical aperture. The method can further include the act of selecting a high-index ball lens based at least in part on one or more of a diameter or an index of refraction of the ball lens. Additionally, the method can comprise the step of arranging the high-index ball lens and the at least two multi-mode fibers within a protective overtube. Additionally, the arranging can include the step of optimizing the distance between the ball lens and the fibers and the distance between respective fibers. These can be optimized to at least one of maximize the overlap between illumination and collection spots, control the beam diameter to be as small as possible, or adopt a large collection angle with respect to the illumination beam. The optimization can employ a Monte Carlo or ray tracing simulation to determine the distances.

What follows is a more detailed discussion of certain systems, methods, and apparatuses associated with aspects of the subject innovation. To aid in the understanding of aspects of the subject innovation, theoretical analysis and experimental results associated with specific experiments that were conducted are discussed herein. However, although for the purposes of obtaining the results discussed herein, specific choices were made as to the selection of various aspects of the experiments and associated setups—such as choice of materials and dimensions for fiber optics and ball lens—the systems and methods described herein can be employed in other contexts, as well. For example, various aspects of the subject innovation can be utilized to perform in vivo assessment of superficial tissue. In some embodiments, different selections of materials, configurations, analytical methods, or dimensions can be selected than those used in the experiments discussed herein, and may have differing characteristics, as explained in greater detail below.

To benchmark the performance of the depth-selective probe, it was compared with a standard reflectance spectroscopy fiber-optic probe that was commercially available and widely used in optical spectroscopy. This standard reflectance probe (SRP) consisted of six illumination fibers and one collection fiber with 200 μm core diameter and the central distance between source and detection fibers was approximately 250 μm. Additionally, to compare the performance of the depth-selective probe with conventional probes known to give relatively short penetration depths, the fiber core diameter of the SRP was reduced to 50 μm, the smallest multi-mode fiber diameter currently used in reflectance spectroscopy. Further, given that angled probes have previously been used to achieve shorter penetration depth, angled probes with collection fibers placed at 15° and 45° with 200 μm fiber core diameter were also used.

Numerical simulations were performed using a Monte Carlo method to determine the penetration depth of the depth-selective probe and other standard reflectance probes. The numerical experiments were designed to ensure that the light collection geometry modeled in the simulations emulated realistic experimental conditions and the output of the numerical simulations was analogous to those typically recorded in experiments.

The numerical experiments followed the protocol of a saturation curve method. In brief, the experiment varied the geometrical thickness D of the sample. For each D, the reflectance signals were recorded for a specific collection radial ranges R according to the design of the fiber-optic probe. As D increases, the reflectance signal first increases and then reaches a plateau at a specific $D_c$, known as the saturation curve. The penetration depth T is defined as the geometrical thickness D such that the saturation curve reaches 90% of its saturation value. In the simulation, the geometrical thickness D was varied from 20 μm to 3000 μm. A wide range of tissue-relevant scattering coefficient $\mu_s$ and absorption coefficient $\mu_a$ were used. The simulations in these experiments used $10^7$ photons.

To validate the penetration depth of the fiber-optic probes determined by Monte-Carlo simulation and saturation-curve method, experiments were performed using tissue phantoms consisting of polystyrene microsphere suspension (with diameter d=4.3 μm±25%, and index of refraction n=1.59). The scattering coefficient $\mu_s$ was calculated based on the concentration of microsphere suspension and Mie theory. To obtain the saturation curve, the probe tip was immersed in the microsphere suspension, and the distance between the probe tip and the bottom of the suspension was gradually increased from 20 μm to 3000 μm via a micrometer-controlled translational stage. The reflectance spectroscopy measurement of $I_s(\lambda)$ was taken at each step. The obtained spectrum $I_s(\lambda)$ was further normalized by using the following scheme in equation (1):

$$R(\lambda) = \frac{I_s(\lambda) - I_{bg}(\lambda)}{I_{ref}(\lambda) - I_{bg}(\lambda)} \quad (1)$$

where $R(\lambda)$ denotes the normalized signal, and $I(\lambda)$, $I_{ref}(\lambda)$ and $I_{bg}(\lambda)$ denotes the measured reflectance signals from the sample, reference and background, respectively. A reflectance standard (99% reflectivity) was used as the reference. The background measurement was taken when the probe tip is immersed in pure water.

A series of tissue phantoms with a range of similar scattering and absorption properties as the soft tissue were used. The human blood was used as the absorber and polystyrene microsphere suspension was used as the turbid scattering medium. A venous blood sample was collected from a healthy volunteer. The sample was collected in an ethylenediaminetetraacetic acid (EDTA)-treated Vacutainer® Blood Collection Tube and subsequently analyzed for hemoglobin concentration using a COULTER® LH 750 Hematology Analyzer (Beckman Instruments). The base blood sample was then added into the polystyrene microsphere suspension, yielding multiple samples of serially increasing hemoglobin concentration differing by about 1 g/L. To quantify the hemoglobin content in tissue phantoms, a modified Beer-Lambert law was used, described as in equation (2):

$$R(\lambda) = I_{scattering}(\lambda) \cdot \exp(-\alpha_{HbO2} \cdot A_{HbO2}(\lambda) - \alpha_{Hb} \cdot A_{Hb}(\lambda)) \quad (2)$$

where $R(\lambda)$ is the experimentally obtained reflectance spectrum as a function of wavelength $\lambda$; $I_{scattering}(\lambda)$ denotes the absorber-free scattering signal of the sample; $A_{HbO2}(\lambda)$ and $A_{Hb}(\lambda)$ denote the absorption spectrum of the oxygenated and deoxygenated hemoglobin, respectively; and $\alpha_{HbO2}$ and $\alpha_{Hb}$ represent the oxygenated and deoxygenated hemoglobin contents. The $I_{scattering}(\lambda)$ was obtained using the simulated curve based on Mie Theory. The $A_{HbO2}(\lambda)$ and $A_{Hb}(\lambda)$ were obtained from published sources. To calculate $\alpha_{HbO2}$ and $\alpha_{Hb}$, the Eq. (2) was fitted given $R(\lambda)$, $I_{scattering}(\lambda)$, $A_{HbO2}(\lambda)$ and $A_{Hb}(\lambda)$. The fitting was optimized by minimizing the sum of square error over the wavelength range of 460-700 nm with the Matlab function fininsearch.

The reflectance spectra from human skin were obtained using both the depth-selective probe and the standard reflectance probe. Three skin sites of an Asian volunteer were evaluated, including finger tip, lip and volar forearm. Six measurements were taken on each site and the averaged spectrum was used as the representative spectrum for each skin site. The final representative spectrum was fitted by equation (3):

$$R(\lambda) = \lambda^{-\beta} \cdot \exp(-\alpha_{HbO2} \cdot A_{HbO2}(\lambda) - \alpha_{Hb} \cdot A_{Hb}(\lambda)) \quad (3)$$

where β denotes the scattering power, and $\alpha_{HbO2}$ and $\alpha_{Hb}$ denote the oxygenated and deoxygenated hemoglobin coefficients, respectively. To derive the values of β, $\alpha_{HbO2}$ and $\alpha_{Hb}$, a fitting method similar to that described above was used.

In general, three major technical factors in a fiber-optic probe can affect its penetration depth: (1) Diameter of illumination and collection spot; (2) Separation distance between the illumination and collection spots; and (3) Angle between illumination beam and collection beam. In various aspects, some or all of these factors can be optimized to select a desired penetration depth (e.g., a short penetration depth, etc.).

To achieve a short penetration depth, some embodiments of the subject innovation can at least one of maximize the overlap between illumination and collection spots while controlling the beam diameter to be as small as possible and/or adopting a large collection angle with respect to the illumination beam. In various embodiments of a depth-selective probe design, all of these three factors can be optimized to result in a short penetration depth while maintaining sufficient light collection efficiency and minimizing the specular reflection. Such embodiments can employ a high-index ball lens (e.g., n=1.85, although greater or lesser values can be used), which can offer a large numerical aperture (e.g., NA≈0.65 for the example probe used in the experiments, although variations in parameters (e.g., n, the geometry of the system, etc.) can result in a greater or lesser NA) and superior focusing capacity, and can adjust the distance between the illumination and collection fibers as well as the distance between the fiber and ball lens in order to reduce penetration depth. The use of a high-index ball-lens can often be accompanied by significant specular reflection due to the multiple reflections at the ball lens-air and fiber-air interfaces, which can contribute to background signals, resulting in reduced signal-to-noise ratio (SNR). The subject innovation can numerically adjust the distance between the illumination and collection fibers as well as the distance between the fiber tip and ball lens to minimize such specular reflection in the background signal in the simulation using simulation or ray tracing software (e.g., TracePro) and optimizing a high collection efficacy of reflectance signal for smaller probing depth.

Figure 2A:
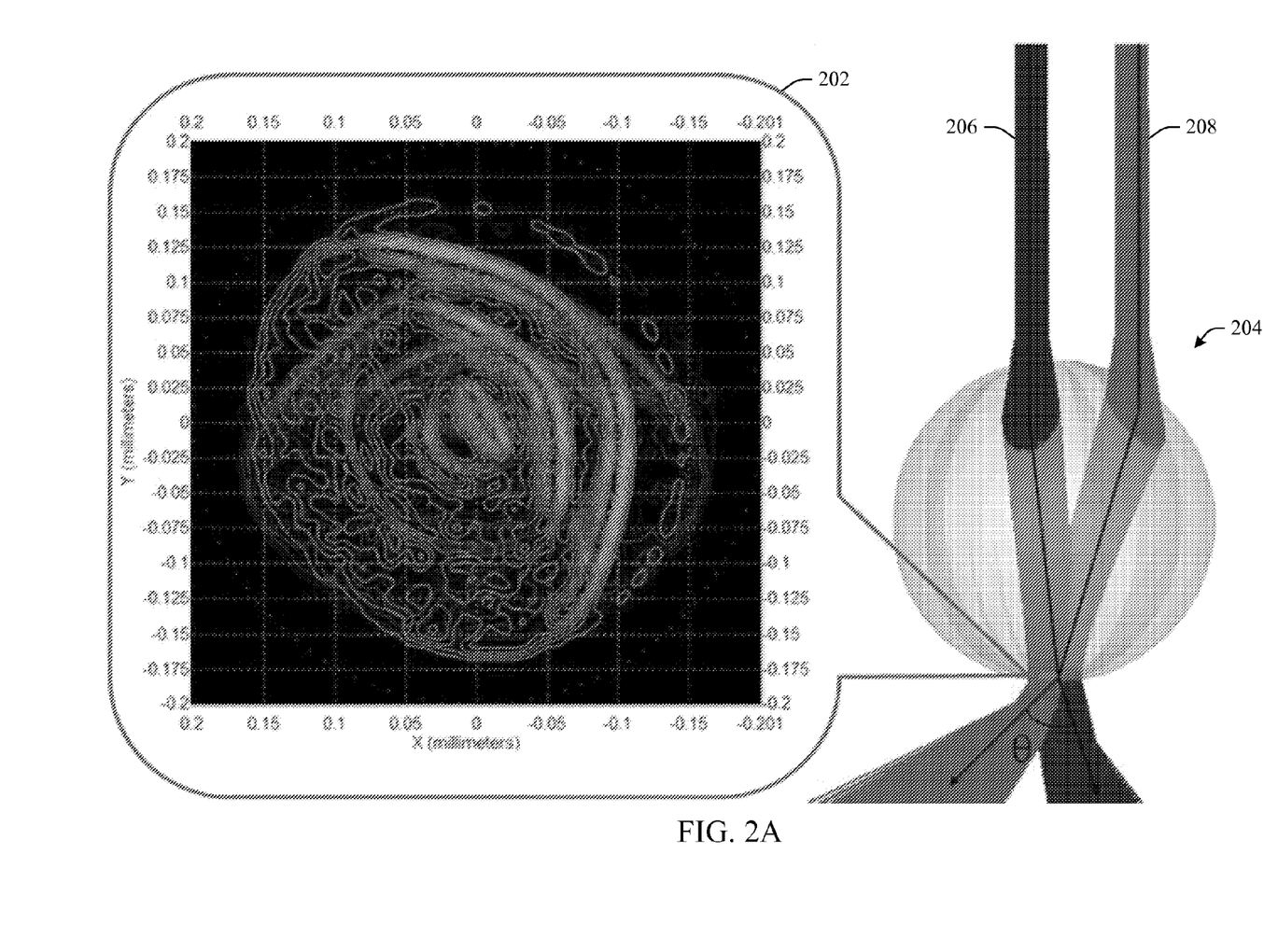
FIG. 2A shows an example intensity contour profile graph and associated system configuration, in accordance with an embodiment of the subject innovation.

FIG. 2A shows an example intensity contour profile graph 202 and associated system configuration 204, with the illumination in blue and collection in red, in accordance with an embodiment of the subject innovation. In some embodiments, the collection and illumination spots at the surface of the probe tip can be controlled to be as small as ~300 μm in diameter, and can have a maximal overlap between the illumination and collection areas. Such embodiments can result in the smallest possible source-detection fiber separation and illumination size, which can provide for the short penetration depth, without a significant sacrifice of light collection efficiency and specular reflection. Additionally, the large angle θ between the illumination beam 206 and the collection beam 206 (e.g., θ=37.4° in air and θ=27.8° in water for an embodiment such as used in the experiments described herein) can further select those photons originating from a short tissue depth.

Figure 2B:
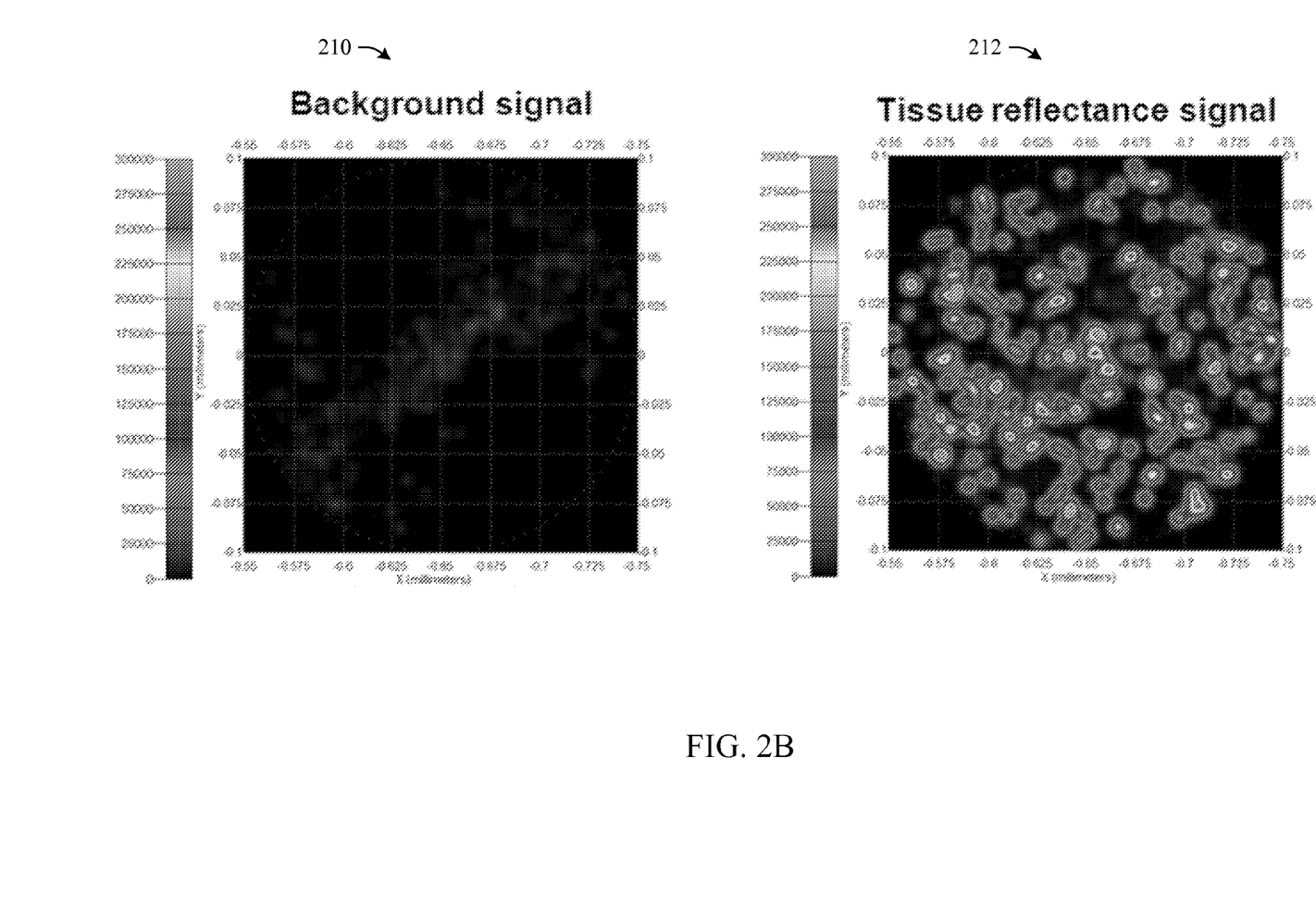
FIG. 2B shows the background and tissue reflectance signals from an example depth-selective probe with 200 μm core fiber diameter, where the color bar represents irradiance (W/m²).

FIG. 2B shows the background signal 210 and tissue reflectance signal 212 from the depth-selective probe with 200 µm core fiber diameter used in the experiments, where the color bar represents irradiance (W/m$^2$). The signal-to-noise ratio was quantified both numerically and experimentally. The tissue reflectance irradiance was simulated using a tissue model (i.e., tissue stratum corneum) selected from the sample library of the software. The SNR of the depth-selective probe used in the experiments (i.e., with 200 µm fiber diameter) was 15.1 dB.

To further compare the reflectance signal collection efficacy for the depth-selective probe that samples a smaller penetration depth with those that sample a much deeper depth, the SNR from the depth-selective probe and that from the commercially available standard reflectance probe (SRP) with the same fiber core diameter of 200 µm were experimentally quantified. The reflectance signals were obtained from the human fingertip. The average SNR for the depth-selective probe (500-700 nm) was ~11.2 dB, while the SRP with 200 µm diameter has an average SNR of ~12.6 dB. Therefore, the SNR for the depth-selective probe maintained about 73% of collection efficiency compared to a SRP with the same diameter. However, considering that the SRP has 6 illumination fibers and one collection fiber, while the 200 µm-diameter depth-selective probe used in the experiments had only one illumination fiber and one collection fiber, the reflectance signal collection efficiency of the depth-selective probe was in fact similar to or even better than the SRP with the same fiber diameter.

Figure 3:
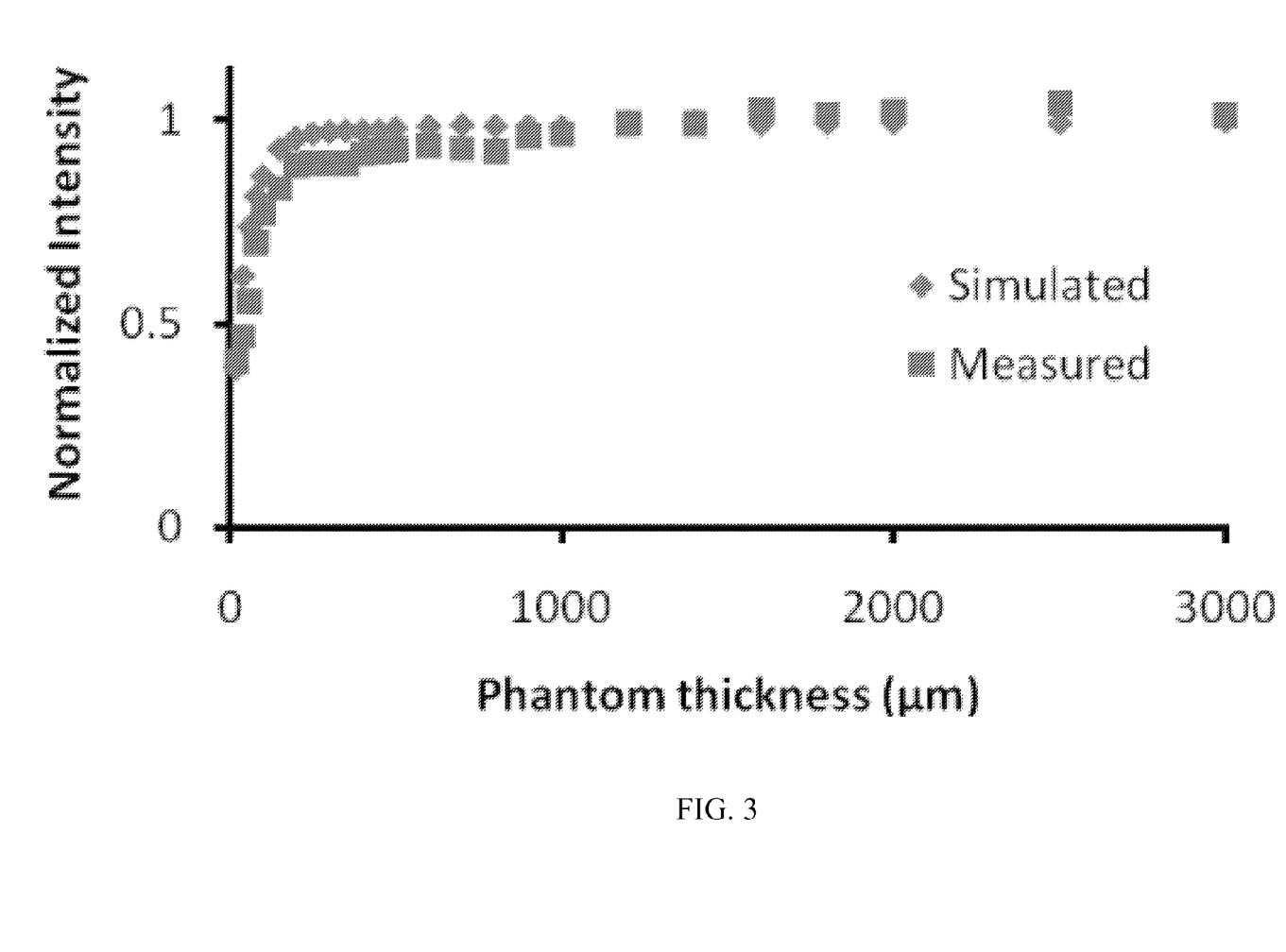
FIG. 3 shows a saturation curve obtained from numerical simulations compared with that from experiments using tissue phantoms consisting of polystyrene microsphere suspension.

FIG. 3 shows the saturation curve obtained from numerical simulations compared with that from experiments using tissue phantoms consisting of polystyrene microsphere suspension, validating the accuracy of the numerical simulation approach in defining the penetration depth. In both the numerical simulations and the experiments illustrated in FIG. 3, $\mu_s$=200 cm$^{-1}$. These simulations characterized the penetration depth of the depth-selective probe and other comparative standard reflectance probes using a series of Monte-Carlo based numerical simulations. As can be seen from FIG. 3, the saturation curve obtained from the numerical simulation shows a good agreement with the experimental result. It can also be seen in FIG. 3 that both numerical simulation and experiments confirmed that the example depth-selective probe used in the experiments selected a very short penetration depth of approximately 200 µm (although different embodiments can have varying penetration depths.

Figure 4:
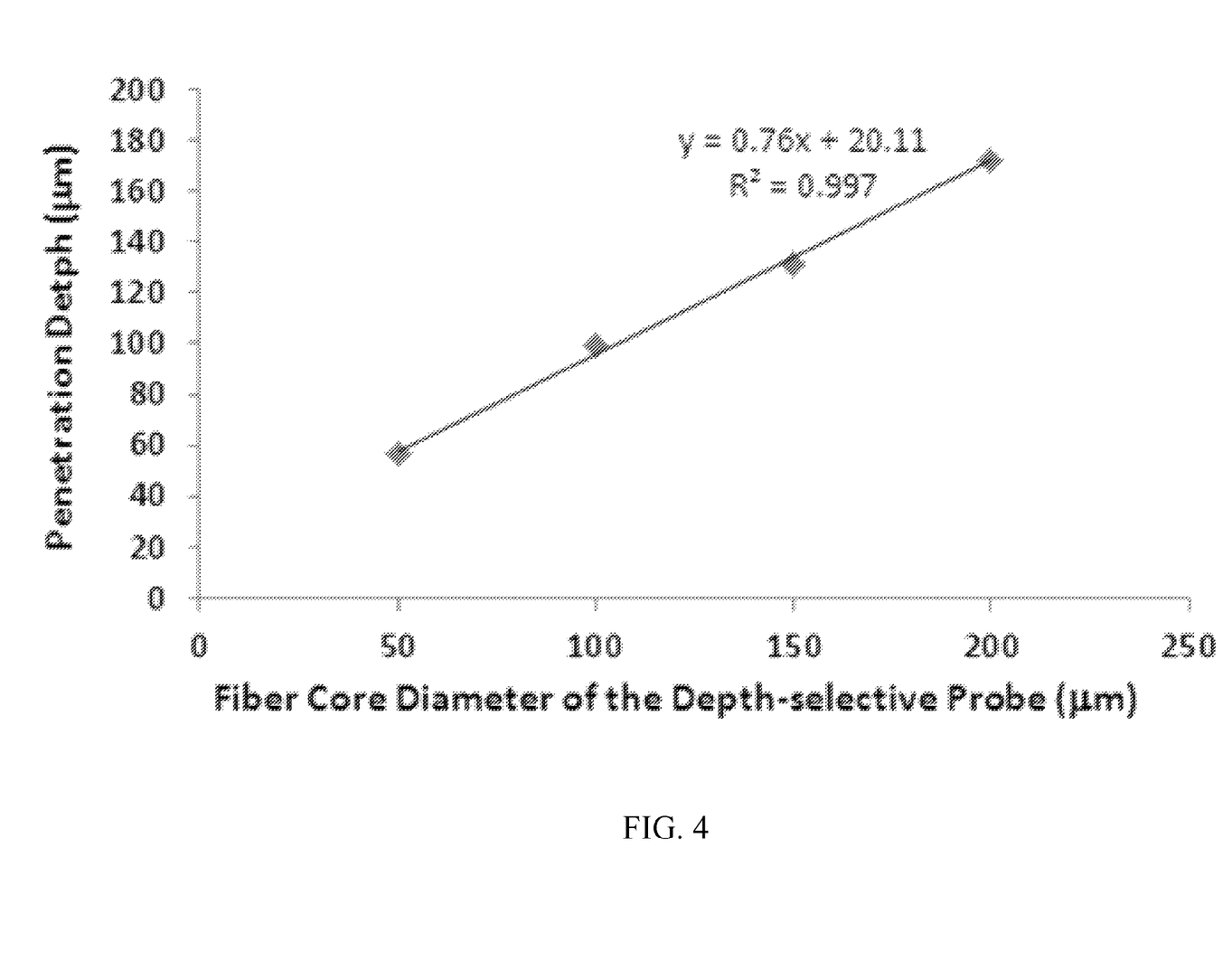
FIG. 4 shows the dependence of sampling depth on the fiber core diameters of a depth-selective probe used in experiments herein.

FIG. 4 shows the dependence of sampling depth on the fiber core diameters of a depth-selective probe used in experiments herein. The scattering coefficient $\mu_s$ was 200 cm$^{-1}$, the anisotropy factor g was 0.87, and the absorption coefficient $\mu_a$ was 5 cm$^{-1}$. This portion of the experiment evaluated the penetration depth of the depth-selective probe with different fiber diameters (50, 100, 150, 200 µm) using the Monte-Carlo simulation in conjunction with the saturation curve analysis. As shown in FIG. 4, the penetration depth was approximately linearly proportional to the fiber diameter. If the fiber diameter size was reduced to 50 µm (one of the smallest available core diameters of multi-mode fibers), the penetration depth could reach approximately 50-60 µm.

The scattering properties of biological tissue can generally be described by two physical parameters: a scattering coefficient $\mu_s$ and an anisotropy factor g. In experiments discussed herein, the effect of scattering coefficient on the penetration depth was evaluated using Monte Carlo simulation and the saturation curve method. The penetration depth of the depth-selective probe was compared with that from two standard reflectance probes (SRPs) with fiber core diameter of 200 µm and 50 µm, respectively.

Figure 5A:
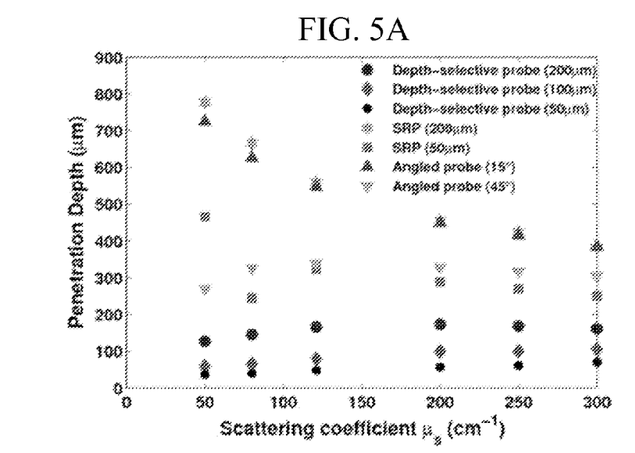
FIG. 5A shows the effect of scattering coefficient on penetration depth in experiments discussed herein.
Figure 5B:
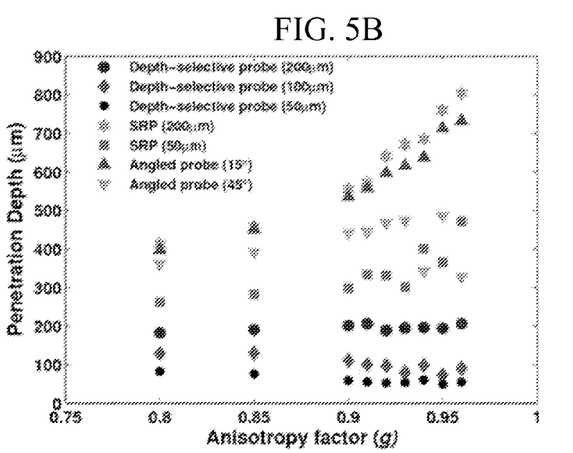
FIG. 5B shows the effect of anisotropy factor on penetration depth in experiments discussed herein.
Figure 5C:
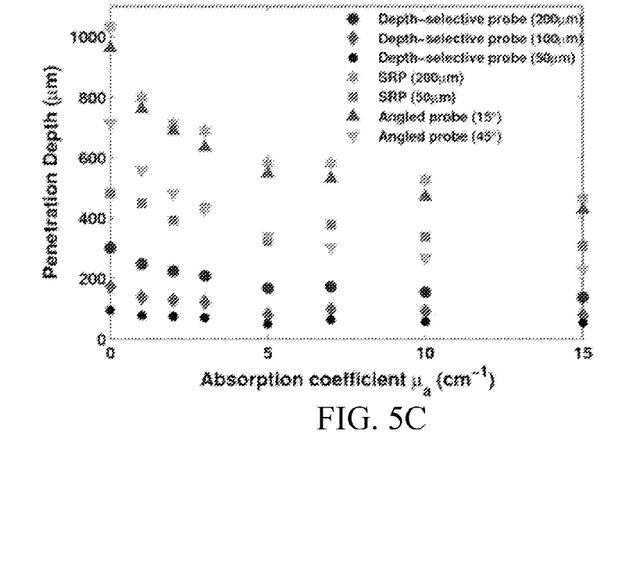
FIG. 5C shows the effect of absorption coefficient on penetration depth in experiments discussed herein.

FIGS. 5A, 5B, and 5C show the effect of scattering coefficient, anisotropy factor g, and absorption coefficient, respectively, in a wide tissue-relevant range. As can be seen in FIG. 5A, the depth-selective probe is insensitive to a range of tissue-relevant scattering coefficients. In contrast, the penetration depth of the SRP with 200 µm or 50 µm shows a much stronger dependence on the scattering coefficient and anisotropy factor. As shown in FIG. 5A, for a wide range of scattering coefficients (50-300 cm$^{-1}$) at constant anisotropy factor g of 0.87 and absorption coefficient $\mu_a$ of 5 cm$^{-1}$, the depth-selective probe can assess a much shallower penetration depth (i.e., less than 200 µm). The performance of the example depth-selective probe (with 200 µm fibers) is even superior to the SRP with the smallest available core diameter of multi-mode fibers (i.e., 50 µm). This result demonstrates the relative importance of maximal overlap between the illumination and collection spots in reducing the penetration depth as compared with the fiber diameter. Similarly, as shown in FIG. 5B, which illustrates penetration depth at a fixed scattering coefficient $\mu_s$ of 200 cm$^{-1}$ and absorption coefficient $\mu_a$ of 5 cm$^{-1}$ for anisotropy factors g ranging from 0.80 to 0.96, the penetration depth of the SRP increases significantly with the increase of anisotropy factor g. However, the depth-selective probe can assess a nearly constant penetration depth in a wide range of anisotropy factor, even in the case of highly forward-directed scattering (e.g., g>0.9), in which a short penetration depth is especially difficult to achieve. These results show that the depth-selective probe can maintain superior performance, with a short and constant physical penetration depth in a very wide range of scattering properties, even for those highly forward-directed scattering media. Additionally, FIG. 5C shows the effect of absorption coefficient on penetration depth in experiments discussed herein, for a fixed scattering coefficient $\mu_s$ of 121 cm$^{-1}$ and anisotropy factor g of 0.87. As shown in FIG. 5C, when the absorption coefficient is small ($\mu_a$<1 cm$^{-1}$), the penetration depth of the depth-selective probe with 200 µm diameter shows a slight dependence on absorption coefficient. Such effect is almost negligible if the fiber diameter is reduced to 100 and 50 µm or when the absorption level ranges from medium to strong ($\mu_a$<2 cm$^{-1}$). Therefore, the depth-selective probe with the smallest available core diameter could achieve the shortest penetration depth and have least sensitivity to a wide range of optical properties.

To demonstrate the potential of the depth-selective probe to accurately determine the absorber concentration in the turbid media, the absorption coefficient of hemoglobin in tissue models was quantified with three different scattering coefficients: 80, 130 and 200 cm$^{-1}$. For each model, the concentration of total hemoglobin was varied from 0 g/L to 15 g/L, with the corresponding absorption coefficient $\mu_a$ ranging from 0 to 13 cm$^{-1}$ at the wavelength of 570 nm.

Figure 6A:
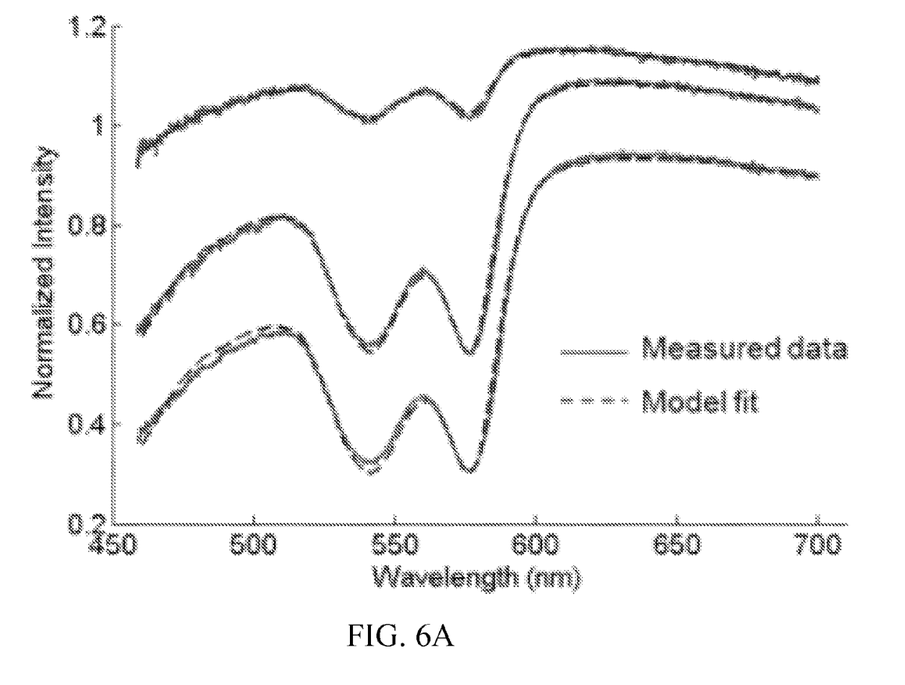
FIG. 6A shows the reflectance spectra obtained with the depth-selective probe and the corresponding fitted spectra in experiments discussed herein.
Figure 6B:
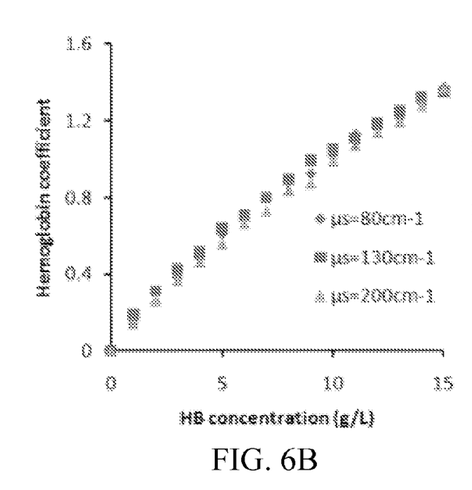
FIG. 6B shows a comparison between the calculated hemoglobin coefficient and the actual hemoglobin concentration from the depth-selective probe.
Figure 6C:
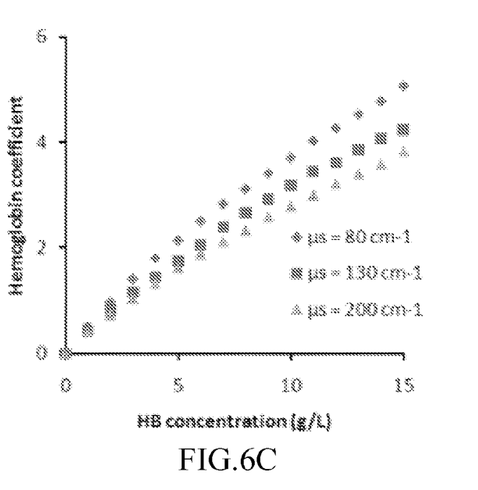
FIG. 6C shows a comparison between the calculated hemoglobin coefficient and the actual hemoglobin concentration from a standard reflectance probe.

FIG. 6A shows the reflectance spectra obtained with the depth-selective probe and the corresponding fitted spectra using the method described above for hemoglobin concentrations of 1 g/L, 8 g/L, and 15 g/L, respectively. As can be seen in FIG. 6A, a good fit can be achieved by the depth-selective probe for a wide range of hemoglobin concentration. FIG. 6B shows a comparison between the calculated hemoglobin coefficient and the actual hemoglobin concentration from the depth-selective probe. As can be seen in FIG. 6B, the calculated hemoglobin coefficient is linearly related to the actual hemoglobin concentration, independent of a wide range of tissue-relevant scattering coefficients. In comparison, FIG. 6C, the calculated hemoglobin coefficient for the SRP with 200 µm core diameter, shows that the determination of hemoglobin coefficient is strongly confounded by the scattering coefficients if the SRP is used. Essentially, the derived hemoglobin coefficients from both probes represent the hemoglobin content within the sampling volume. The depth-selective probe assesses a relatively constant optical path length (or sampling volume), while the assessing optical path length from the SRP probe is very sensitive to the scattering coefficient, which results in inaccurate estimation of hemoglobin concentration. These results demonstrate the potential of the depth-selective probe in unambiguous determination of absorber concentration in turbid media.

Figure 7:
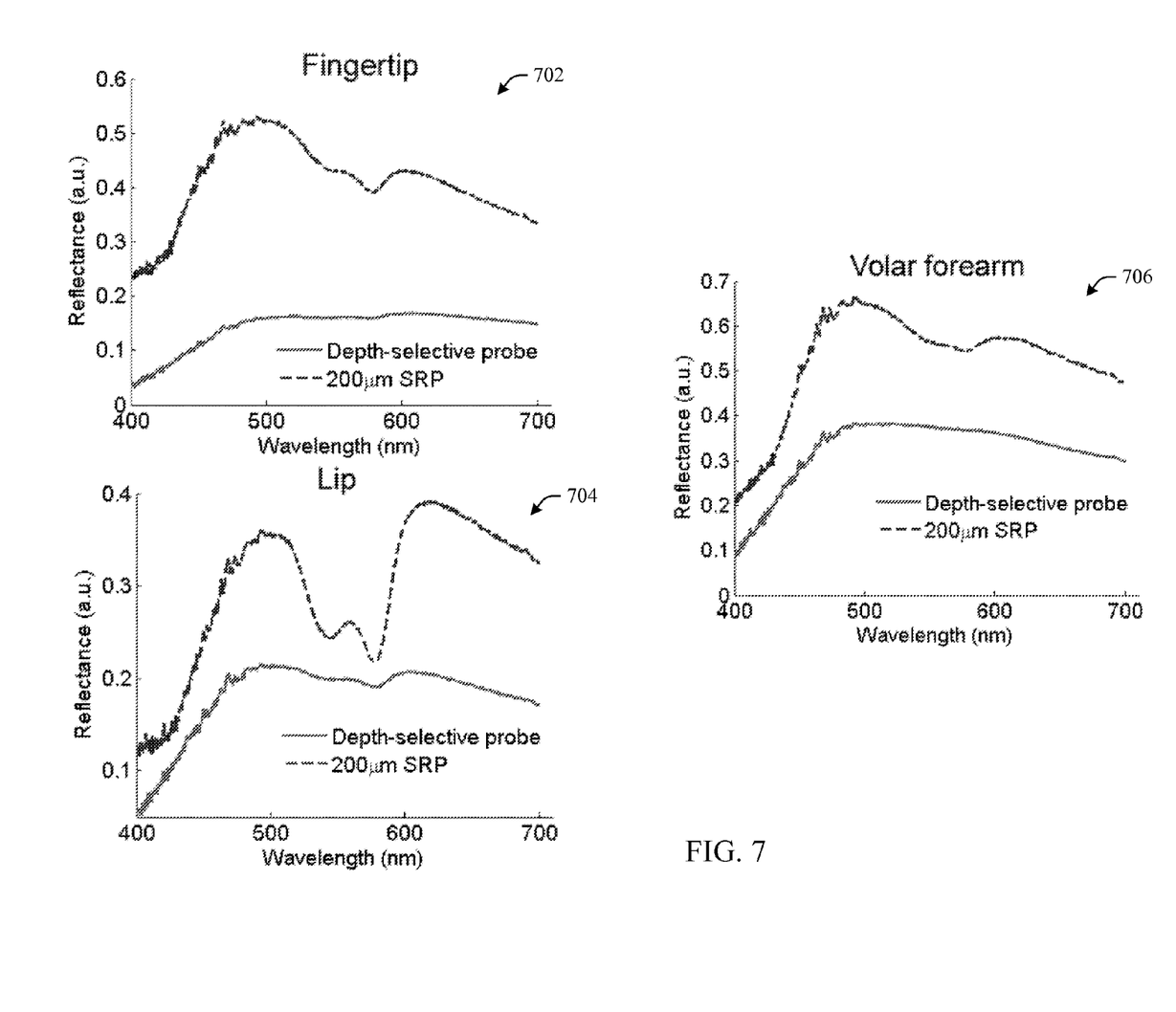
FIG. 7 illustrates representative reflectance spectra from three skin tissue sites based on experiments discussed herein.

FIG. 7 illustrates representative reflectance spectra from three skin tissue sites. As discussed, the experiments further explored the capability of the depth-selective probe to evaluate the reflectance spectra of multi-layered tissue. Three human skin tissue sites were evaluated: finger tip, lip and volar forearm. These three skin sites are representative of distinct tissue properties at different tissue layers: Finger tip consists of a very thick (a few hundred microns) and highly-scattered superficial layer of stratum corneum with a highly dense vascular network underneath the epidermis. Lip is also a highly vascular site but with a very thin layer (only a few microns) of stratum corneum. The volar forearm has approximately 20 µm thickness of stratum corneum underneath which the blood vessels are less dense than those in the lip and finger tip. FIG. 7 shows the representative reflectance spectra from these three skin tissue sites, obtained with both depth-selective probe, in red, and SRP (200 µm diameter), in blue. The reflectance spectrum from finger tip obtained with the depth-selective probe shows very little hemoglobin absorption features, in distinct contrast to the strong hemoglobin absorption shown in the reflectance spectrum obtained with the SRP, as shown in graph 702. This result implies that the depth-selective probe indeed assesses a very short penetration depth, approximately within the thickness of stratum corneum and epidermis of ~200 µm. In addition, in the spectral range of 630-700 nm, the reflectance spectrum with the depth-selective probe is nearly flat, but the spectrum with the SRP shows a strong declining slope in part due to the contribution of the hemoglobin absorption from the deeper tissue. On the other hand, lip has a much thinner stratum corneum of only several microns. Although the reflectance spectra from the lip obtained with both probes, seen in graph 704, show the hemoglobin absorption characteristics, the spectrum with the depth-selective probe shows a significantly lesser amount of hemoglobin absorption. Furthermore, the reflectance spectra from the volar forearm in graph 706 show almost no hemoglobin absorption when the depth-selective probe is used, due to the small amount of vasculature in the superficial skin.

Major tissue properties were further quantified by fitting equation (3) in the spectral range from 520 nm to 700 nm as described above, and the scattering power β, oxygenated hemoglobin coefficient [$\alpha_{HbO2}$] and deoxygenated hemoglobin coefficient [$\alpha_{Hb}$] were determined with the depth-selective probe and SRP, and tabulated in Table 1:

TABLE 1

Major tissue properties of three skin sites

| | Depth-selective probe | | | SRP with 200 µm diameter | | |
|---|---|---|---|---|---|---|
| | β | $\alpha_{HbO2}$ | $\alpha_{Hb}$ | β | $\alpha_{HbO2}$ | $\alpha_{Hb}$ |
| Finger tip | 0.50 | 1.6E−06 | 2.8E−07 | 1.69 | 2.2E−06 | 1.7E−06 |
| Lip | 0.93 | 2.2E−06 | 7.3E−07 | 1.24 | 8.8E−06 | 5.4E−06 |
| Volar forearm | 0.88 | ≈0 | ≈0 | 1.22 | 1.1E−06 | 2.1E−06 |

As can be seen in Table 1, the hemoglobin coefficients assessed with the depth-selective probe are significantly less than those from the SRP, due to its small sampling volume and avascular nature of the superficial skin. Also notable are the significantly distinct results of scattering power β using two different types of probes. With the depth-selective probe, the finger tip shows the smallest value of β, but this value is the largest with the SRP. The smaller value of β is generally related to a larger scatterers' size. The smaller value of β with the depth-selective probe is consistent with the presence of large cells in the stratum corneum of finger tip. The results shown in Table 1 underlie the importance of evaluating superficial skin tissue properties in a depth-selective manner.

In various aspects, the innovation includes a compact and simple fiber-optic depth-selective probe (e.g., two-channel, etc.) that can be used for in vivo assessment of superficial tissue. Various embodiments of depth-selective probes can efficiently incorporate one or more approaches that can limit the penetration depth, such as: reducing illumination spot size, reducing separation distance between illumination and collection areas, and enlarging collection angle. These can be accomplished via a fiber-coupling high-index ball lens and appropriate positioning of fibers and fiber-lens distance, while maintaining sufficient light collection efficiency without specular reflection. The depth selectivity of an example embodiment of a depth-selective probe was evaluated by both experiments and numerical simulations discussed herein. These showed that the example probe selects a very short physical penetration depth of approximately 200 µm. One notable characteristic of this depth-selective probe is its ability to assess a constant physical depth that is independent of a very wide range of scattering coefficient and anisotropy factor values. Furthermore, with the depth-selective probe, the determination of the absorber concentration in turbid media can avoid being confounded by a wide range of tissue-relevant scattering coefficients. The capability of the depth-selective probe for in vivo tissue assessment was further demonstrated in multi-layered skin tissue with three distinct tissue sites. The reflectance spectra obtained with the depth-selective probe provide dramatically different information about tissue properties compared to those obtained with a standard reflectance spectroscopy probe. The quantification of absorption and scattering properties of the superficial tissue can be significantly biased without the depth-selective evaluation. Systems and methods of the subject innovation are useable in a broad range of biomedical applications, such as endoscopic tissue assessment (embodiments of the subject innovation can be readily included in endoscopes due to the small probe sizes, e.g., 2 mm, of these embodiments), characterization of superficial skin pigmentation, and evaluation of the effect of therapeutic or cosmetic agents on superficial tissue. Analysis of superficial tissue by various embodiments of the subject innovation can be used to detect a range of conditions, from cosmetic (e.g., moisturization, etc.) to pathological (e.g., cancer detection, etc.).

Figure 8:
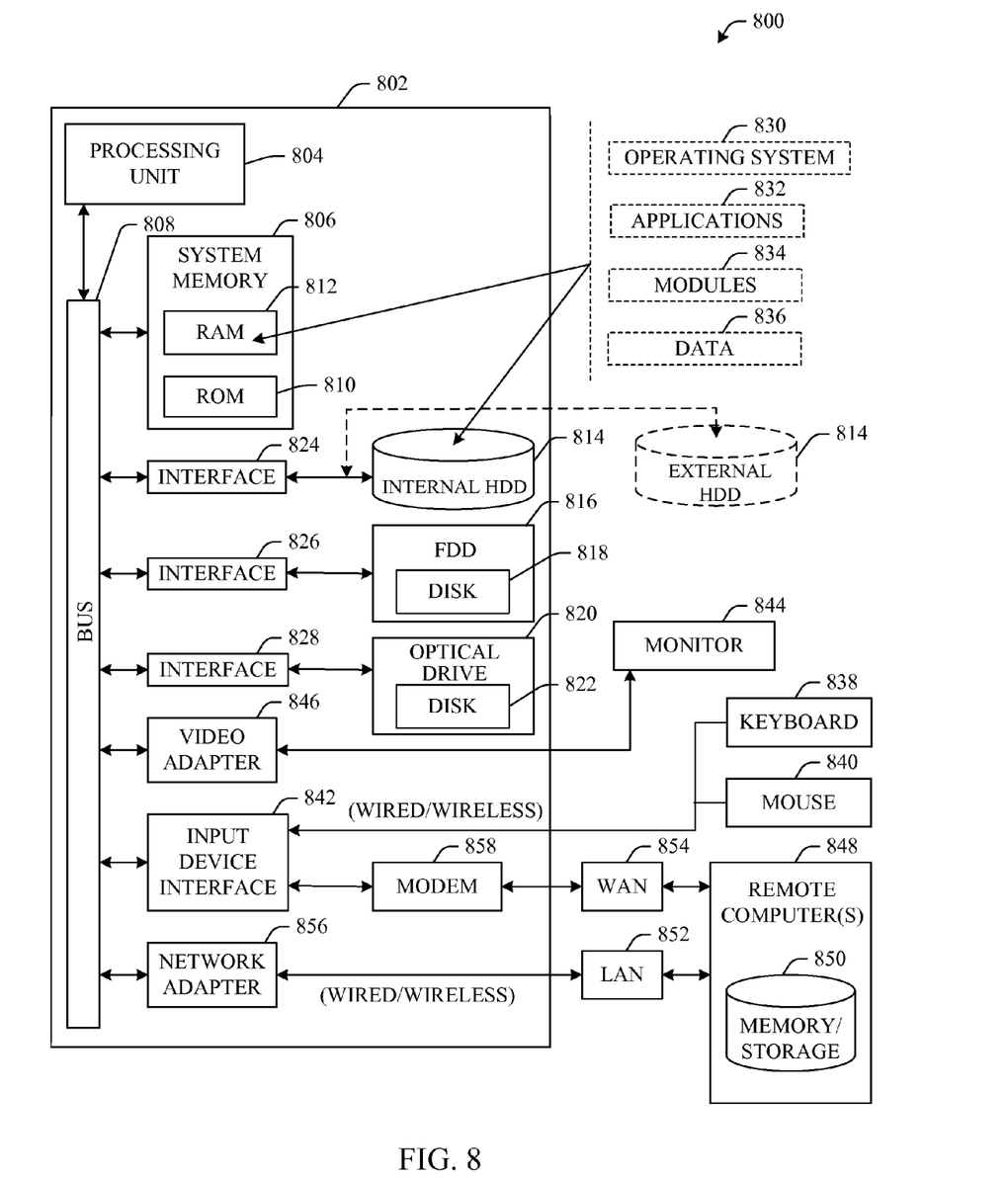
FIG. 8 illustrates a block diagram of a computer operable to execute the disclosed architecture.

Referring now to FIG. 8, there is illustrated a block diagram of a computer operable to execute the disclosed architecture. In order to provide additional context for various aspects of the subject innovation, FIG. 8 and the following discussion are intended to provide a brief, general description of a suitable computing environment 800 in which the various aspects of the innovation can be implemented. While the innovation has been described above in the general context of computer-executable instructions that may run on one or more computers, those skilled in the art will recognize that the innovation also can be implemented in combination with other program modules and/or as a combination of hardware and software.

Generally, program modules include routines, programs, components, data structures, etc., that perform particular tasks or implement particular abstract data types. Moreover, those skilled in the art will appreciate that the inventive methods can be practiced with other computer system configurations, including single-processor or multiprocessor computer systems, minicomputers, mainframe computers, as well as personal computers, hand-held computing devices, microprocessor-based or programmable consumer electronics, and the like, each of which can be operatively coupled to one or more associated devices.

The illustrated aspects of the innovation may also be practiced in distributed computing environments where certain tasks are performed by remote processing devices that are linked through a communications network. In a distributed computing environment, program modules can be located in both local and remote memory storage devices.

A computer typically includes a variety of computer-readable media. Computer-readable media can be any available media that can be accessed by the computer and includes both volatile and nonvolatile media, removable and non-removable media. By way of example, and not limitation, computer-readable media can comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or any other medium which can be used to store the desired information and which can be accessed by the computer.

Communication media typically embodies computer-readable instructions, data structures, program modules or other data in a modulated data signal such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer-readable media.

With reference again to FIG. 8, the exemplary environment 800 for implementing various aspects of the innovation includes a computer 802, the computer 802 including a processing unit 804, a system memory 806 and a system bus 808. The system bus 808 couples system components including, but not limited to, the system memory 806 to the processing unit 804. The processing unit 804 can be any of various commercially available processors. Dual microprocessors and other multi-processor architectures may also be employed as the processing unit 804.

The system bus 808 can be any of several types of bus structure that may further interconnect to a memory bus (with or without a memory controller), a peripheral bus, and a local bus using any of a variety of commercially available bus architectures. The system memory 806 includes read-only memory (ROM) 810 and random access memory (RAM) 812. A basic input/output system (BIOS) is stored in a non-volatile memory 810 such as ROM, EPROM, EEPROM, which BIOS contains the basic routines that help to transfer information between elements within the computer 802, such as during start-up. The RAM 812 can also include a high-speed RAM such as static RAM for caching data.

The computer 802 further includes an internal hard disk drive (HDD) 814 (e.g., EIDE, SATA), which internal hard disk drive 814 may also be configured for external use in a suitable chassis (not shown), a magnetic floppy disk drive (FDD) 816, (e.g., to read from or write to a removable diskette 818) and an optical disk drive 820, (e.g., reading a CD-ROM disk 822 or, to read from or write to other high capacity optical media such as the DVD). The hard disk drive 814, magnetic disk drive 816 and optical disk drive 820 can be connected to the system bus 808 by a hard disk drive interface 824, a magnetic disk drive interface 826 and an optical drive interface 828, respectively. The interface 824 for external drive implementations includes at least one or both of Universal Serial Bus (USB) and IEEE 1394 interface technologies. Other external drive connection technologies are within contemplation of the subject innovation.

The drives and their associated computer-readable media provide nonvolatile storage of data, data structures, computer-executable instructions, and so forth. For the computer 802, the drives and media accommodate the storage of any data in a suitable digital format. Although the description of computer-readable media above refers to a HDD, a removable magnetic diskette, and a removable optical media such as a CD or DVD, it should be appreciated by those skilled in the art that other types of media which are readable by a computer, such as zip drives, magnetic cassettes, flash memory cards, cartridges, and the like, may also be used in the exemplary operating environment, and further, that any such media may contain computer-executable instructions for performing the methods of the innovation.

A number of program modules can be stored in the drives and RAM 812, including an operating system 830, one or more application programs 832, other program modules 834 and program data 836. All or portions of the operating system, applications, modules, and/or data can also be cached in the RAM 812. It is appreciated that the innovation can be implemented with various commercially available operating systems or combinations of operating systems.

A user can enter commands and information into the computer 802 through one or more wired/wireless input devices, e.g., a keyboard 838 and a pointing device, such as a mouse 840. Other input devices (not shown) may include a microphone, an IR remote control, a joystick, a game pad, a stylus pen, touch screen, or the like. These and other input devices are often connected to the processing unit 804 through an input device interface 842 that is coupled to the system bus 808, but can be connected by other interfaces, such as a parallel port, an IEEE 1394 serial port, a game port, a USB port, an IR interface, etc.

A monitor 844 or other type of display device is also connected to the system bus 808 via an interface, such as a video adapter 846. In addition to the monitor 844, a computer typically includes other peripheral output devices (not shown), such as speakers, printers, etc.

The computer 802 may operate in a networked environment using logical connections via wired and/or wireless communications to one or more remote computers, such as a remote computer(s) 848. The remote computer(s) 848 can be a workstation, a server computer, a router, a personal computer, portable computer, microprocessor-based entertainment appliance, a peer device or other common network node, and typically includes many or all of the elements described relative to the computer 802, although, for purposes of brevity, only a memory/storage device 850 is illustrated. The logical connections depicted include wired/wireless connectivity to a local area network (LAN) 852 and/or larger networks, e.g., a wide area network (WAN) 854. Such LAN and WAN networking environments are commonplace in offices and companies, and facilitate enterprise-wide computer networks, such as intranets, all of which may connect to a global communications network, e.g., the Internet.

When used in a LAN networking environment, the computer 802 is connected to the local network 852 through a wired and/or wireless communication network interface or adapter 856. The adapter 856 may facilitate wired or wireless communication to the LAN 852, which may also include a wireless access point disposed thereon for communicating with the wireless adapter 856.

When used in a WAN networking environment, the computer 802 can include a modem 858, or is connected to a communications server on the WAN 854, or has other means for establishing communications over the WAN 854, such as by way of the Internet. The modem 858, which can be internal or external and a wired or wireless device, is connected to the system bus 808 via the serial port interface 842. In a networked environment, program modules depicted relative to the computer 802, or portions thereof, can be stored in the remote memory/storage device 850. It will be appreciated that the network connections shown are exemplary and other means of establishing a communications link between the computers can be used.

The computer 802 is operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, restroom), and telephone. This includes at least Wi-Fi and Bluetooth™ wireless technologies. Thus, the communication can be a predefined structure as with a conventional network or simply an ad hoc communication between at least two devices.

Wi-Fi allows connection to the Internet from a couch at home, a bed in a hotel room, or a conference room at work, without wires. Wi-Fi is a wireless technology similar to that used in a cell phone that enables such devices, e.g., computers, to send and receive data indoors and out; anywhere within the range of a base station. Wi-Fi networks use radio technologies called IEEE 802.11 (a, b, g, etc.) to provide secure, reliable, fast wireless connectivity. A Wi-Fi network can be used to connect computers to each other, to the Internet, and to wired networks (which use IEEE 802.3 or Ethernet). Wi-Fi networks operate in the unlicensed 2.4 and 5 GHz radio bands, at an 11 Mbps (802.11a) or 54 Mbps (802.11b) data rate, for example, or with products that contain both bands (dual band), so the networks can provide real-world performance similar to the basic 10BaseT wired Ethernet networks used in many offices.

What has been described above includes examples of the innovation. It is, of course, not possible to describe every conceivable combination of components or methodologies for purposes of describing the subject innovation, but one of ordinary skill in the art may recognize that many further combinations and permutations of the innovation are possible. Accordingly, the innovation is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A fiber-optic probe that facilitates characterization of superficial tissue, comprising:
    an illumination fiber, wherein the illumination fiber is a multi-mode optic fiber;
    a collection fiber, wherein the collection fiber is a multi-mode optic fiber;
    a ball lens that couples the illumination fiber and collection fiber; and
    a protective overtube that houses the illumination fiber, the collection fiber, and the ball lens, wherein the arrangement of the illumination fiber, the collection fiber, and the ball lens facilitates a constant penetration depth and are arranged based on an optimization of a first diameter of an illumination spot, a second diameter of a collection spot, a separation distance between the illumination spot and the collection spot, and an angle between an illumination beam and a collection beam, wherein the optimization maximizes an overlap between an illumination area of the illumination fiber and a collection area of the collection fiber.

2. The probe of claim 1, further comprising a spectrometer that facilitates analysis of one or more signals collected via the collection fiber.

3. The probe of claim 1, further comprising an illumination source coupled to the illumination fiber, wherein the illumination source facilitates illumination of the superficial tissue via the illumination fiber and the ball lens.

4. The probe of claim 1, wherein the optimization is based at least in part on a Monte Carlo or ray tracing simulation of photon trajectories associated with the probe.

5. The probe of claim 1, wherein the illumination fiber and the collection fiber each have a core fiber diameter of between 50 μm and 200 μm.

6. The probe of claim 1, wherein the ball lens has an index of refraction of 1.85.

7. The probe of claim 1, wherein the ball lens has a diameter of 2 mm.

8. The probe of claim 1, wherein the distance between the illumination and collection fibers is 0.625 mm and the distance between the ball lens and the illumination and collection fibers is 0.563 mm.

9. The probe of claim 1, wherein the penetration depth is independent of a scattering coefficient and an anisotropy factor.

10. The probe of claim 1, wherein the probe has a penetration depth less than or equal to 200 μm.

11. A method of fabricating a depth-selective probe, comprising:
- selecting at least two multi-mode fibers based at least in part on one or more properties of the at least two multi-mode fibers, wherein the at least two multi-mode fibers comprise an illumination fiber and a collection fiber;
- selecting a high-index ball lens; and
- arranging the high-index ball lens and the at least two multi-mode fibers within a protective overtube, wherein the high-index ball lens couples the at least two multi-mode fibers, the arranging comprising:
  - optimizing a distance between the ball lens and the at least two multi-mode fibers;
  - optimizing the distance between the at least two multi-mode fibers; and
  - optimizing a signal to noise ratio of the depth-selective probe; wherein the optimizations include:
    - minimizing a spot size of the illumination fiber;
    - minimizing specular reflection;
    - maximizing an overlap between an illumination area of the illumination fiber and a collection area of the collection fiber; and
    - maximizing a collection angle with respect to an illumination beam.

12. The method of claim 11, wherein the arranging comprises employing a Monte Carlo simulation or ray tracing simulation of photon trajectories associated with the probe.

13. The method of claim 11, wherein the ball lens has an index of refraction of 1.85.

14. The method of claim 11, wherein the illumination fiber and the collection fiber each have a core fiber diameter of between 50 µm and 200 µm.

* * * * *